(12) United States Patent
Murray

(10) Patent No.: US 7,012,086 B1
(45) Date of Patent: Mar. 14, 2006

(54) TREATMENT OF RETROVIRUS INDUCED DERANGEMENTS WITH NIACIN COMPOUNDS

(75) Inventor: Michael F. Murray, Stoneham, MA (US)

(73) Assignee: The Foundation For Innovative Therapies, Inc., Boston, MA (US)

(*) Notice: Subject to any disclaimer, the term of this patent is extended or adjusted under 35 U.S.C. 154(b) by 0 days.

(21) Appl. No.: 09/609,552

(22) Filed: Jun. 30, 2000

(51) Int. Cl.
*A61K 31/44* (2006.01)
*A61K 31/70* (2006.01)

(52) U.S. Cl. ........................... 514/356; 514/50
(58) Field of Classification Search ............... 514/356, 514/50
See application file for complete search history.

(56) References Cited

U.S. PATENT DOCUMENTS

| | | | |
|---|---|---|---|
| 4,724,232 A * | 2/1988 | Rideout et al. ............... | 514/50 |
| 4,911,917 A | 3/1990 | Kuhrts ........................ | 424/10 |
| 5,023,245 A | 6/1991 | Kuhrts ........................ | 514/54 |
| 5,045,537 A | 9/1991 | Weidmann ................... | 514/63 |
| 5,047,427 A | 9/1991 | Williamson ................ | 514/557 |
| 5,214,062 A | 5/1993 | Mark et al. .................. | 514/309 |
| 5,508,271 A | 4/1996 | Rabinoff ..................... | 514/52 |
| 5,716,946 A | 2/1998 | DeLuca | |
| 5,785,977 A | 7/1998 | Breithbarth ................ | 424/401 |
| 5,916,906 A | 6/1999 | Shaskan ..................... | 514/356 |
| 5,965,167 A | 10/1999 | Sanghvi et al. ............. | 424/490 |
| 5,973,224 A | 10/1999 | Fuchs et al. ................ | 800/200 |
| 5,985,339 A | 11/1999 | Kamarei ..................... | 426/72 |
| 6,020,333 A | 2/2000 | Berque ....................... | 514/251 |
| 6,020,351 A | 2/2000 | Pero ........................... | 514/355 |

OTHER PUBLICATIONS

Murray et al, Biochemical and Biophysical Res. Comm., vol. 210(3), pp. 954-959, 1995.*
Tang et al, Am. J. Epidim., vol. 138(11), pp. 937-951, 1993.*
The Merck Manual of Medical Information, Berkow et al Eds. Merck, Dohm & Sharp, pp. 715, 722-723, 1997.*
Brown et al, Kynurenine and Serotonin Pahtways, pp. 425-435, 1991.*
Tang Alice M., et al., Dietary Micronutrient Intake and Risk of Progression to Acquired Immunodeficiency Syndrome (AIDS) in Human Immunodeficiency Virus Type 1 (HIV-1)-Infected Homosexual Men, Amer. J. of Epidem., vol. 138, No. 11, 932-951 (1993).
Tang Alice M., Graham Neil MH, Saah Alfred J., Effects of Micronutrient Intake on Survival in Human Immunodeficiency Virus Type 1 Infection, Amer. J. of Epidem., vol. 143, No. 12, 1244-1256 (1996).
Krasilnikov NN, et al., Inhibitors of ADP-Ribosylation as Antiviral Drugs: Experimental Study on the Model of HIV Infection (1990).
Petley A., et al., The Pharmacokinetics of Nicotinamide in Humans and Rodents, Diabetes, 44:152-155 (1995).
Dipalma Jr., Thayer WS, Use of Niacin as a Drug, Ann. Rev. Nutr. 11:169-187 (1991).

(Continued)

*Primary Examiner*—Shengjun Wang
(74) *Attorney, Agent, or Firm*—Ellis & Venable, P.C.; Joseph R. Meaney

(57) ABSTRACT

Chronic infection with retroviruses, such as HIV, induce a number of metabolic derangements. The present invention relates to a method for treating retrovirus-infected subjects with niacin compounds to reverse infection induced metabolic derangements.

11 Claims, 4 Drawing Sheets

Baseline Infectious Disease Characteristics of Nicotinamide Study Patients.

| Patient | CD4 count | Antiretroviral [duration] | Co-infections |
|---|---|---|---|
| 1 | 0 | none | molluscum contagiousum |
| 2 | 220 | $PI^1/RTI^2$ [3 years] | none |
| 3 | 290 | RTI [2 years] | none |
| 4 | 620 | none | herpes zoster |

OTHER PUBLICATIONS

Gisslen M., Larson M., Norkrans F., Fuchs D., Wachter H., Hagberg L., Tryptophan Concentrations Increase in Cerebrospinal Fluid and Blood After Zidovudine Treatment in Patients with HIV Type I Infection, AIDS Research and Human Retroviruses, 10(8): 947-951 (1994).

RR Brown, et al., Implications of Interferon Induced Tryptophan Catabolism in Cancer, Autoimmune Disease and AIDS, Kynuronine and Serotin Pathways, 425-435 (1991).

Murray MF, Nghiem M., Srinivasan A., HIV Infection Decreases Intracellular Nicotinamide Adenine Dinucleotide [NAD], Biochemical and Biophysical Research Communications, 212:126-131 (1995).

Murray MF, Srinivasan A., Nicotinamide Inhibits HIV-1 in Both Acute and Chronic In Vitro Infection, Biochemical and Biophysical Research Communications, (3), 210:954-959 (1995).

Skurnick JH, et al., Micronutrient Profiles in HIV-1 Infected Heterosexual Adults, J. Acquir. Immune. Defic. Syndr. Hum. Retrovirol, 12(1):75-83, (1996).

Murray MF, Niacin as a Potential AIDS Preventive Factor, Medical Hypotheses, 53(5):375-379 (1999).

Savarino A., et al., Apoptotic DNA Fragmentation, and its In Vitro Prevention by Nicotinamide, in Lymphocytes from HIV-1 Seropositive Patients and in HIV-1-Infected MT-4 Cells, Cell Biochem. And Funct., vol. 15:171-179 (1997).

Savarino A., et al., Investigation of the Potential Role of Membrane CD38 in Protection Against Cell Death Induced by HIV-1, J. Biolog. And Homeostat. Agents, vol. 10, No. 1, pp. 13-18 (1996).

Casey S. Fu, Marian E. Swendseid, Robert A. Jacob, Ralph W. McKee, Biochemical Markers for Assessment of of Niacin Status in Young Men: Levels of Erythrocyte Niacin Coenzymes and Plasma Tryptophan, in the American Institute of Nutrition, 1989.

Werner ER, Fuchs D, Hausen A, et al. Tryptophan Degradation in Patients Infected by Human Immunodeficiency Virus, Biol Chem Hoppe Seyler 1988: 369(5):337-40.

Larsson M, Hagberg L, Norkrans G, Forsman A, Indole Amine Deficiency in Blood and Cerebrospinal Fluid From Patients With Human Immunodeficiency Virus Infection, J Neurosci Res, 1989; 23(4):441-6.

Fuchs D, Moller AA, Reibnegger G, Stockle E, Werner ER, Wachter H, Decreased serum Tryptophan in Patients With HIV-1 Infection Correlates With Increased Serum Neopterin and with Neurologic/psychiatric Symptoms, J Acquir Immune Defic Syndr, 1990; 3(9):873-6.

Fuchs D, Forsman A, Hagberg L, et al. Immune Activation and Decreased Tryptophan in Patients with HIV-1 Infection, J Interferon Res, 1990; 10(6):599-603.

Fuchs D, Moller AA, Reibnegger G, et al., Increased Endogenous Interferon-Gamma and Neopterin Correlate with Increased Degradation of Tryptophan in Human Immunodeficiency Virus Type 1 Infection, Immunol Lett, 1991; 28(3):207-11.

Heyes MP, Brew BJ, Saito K, et al. Inter-relationships between Quinolinic Acid, Neuroactive Kynurenines, Neopterin and Beta 2-Microglobulin in Cerebrospinal Fluid and Serum of HIV-1-Infected Patients, J Neuroimmunol 1992; 40(1):71-80.

Hortin GL, Landtm, Powderly WG, Changes in Plasma Amino Acid Concentrations in Response to HIV-1 Infection, Clin Chem 1994; 40(5):785-9.

Laurichesse H, Tauverson I. Gourdon F, et al. Threonine and Methionine are Limiting Amino Acids for Protein Synthesis in Patients with AIDS, J Nutr 1998; 128(8): 1342-8.

Huengsberg M, Winer JB, Gompels M, Round R, Ross J, Shahmanesh M, Serum Kynurenine-to-tryptophan Ratio Increases with Progressive Disease in HIV-Infected Patients, Clin Chem 1998; 44(4): 858-62.

Fu Casey S, Swendseid M, Jacob Robert, McKee Ralph, Biochemical Markers for Assessment of Niacin Status in Young Men: Levels of Erythrocyte Niacin Coenzymes and Plasma Tryptophan, American Institute of Nutrition, 1989, 1949-1955.

* cited by examiner

Table 1 - Baseline Infectious Disease Characteristics of Nicotinamide Study Patients.

| Patient | CD4 count | Antiretroviral [duration] | Co-infections |
|---|---|---|---|
| 1 | 0 | none | molluscum contagiousum |
| 2 | 220 | PI[1]/RTI[2] [3 years] | none |
| 3 | 290 | RTI [2 years] | none |
| 4 | 620 | none | herpes zoster |

Table 2 - Baseline Dietary Characteristics of Nicotinamide Study Patients. Daily intake for tryptophan and niacin by dietary survey
[i.e. these numbers reflect the total non-pharmacologic amounts included in participants food and nutritional supplements.]

| Patient | Tryptophan [daily intake] | Niacin [RDA%] |
|---|---|---|
| 1 | 0.89 gms | 42.0 mg [210%] |
| 2 | 1.44 gms | 22.4 mg [112%] |
| 3 | 0.66 gms | 32.8 mg [164%] |
| 4 | 1.05 gms | 24.0 mg [120%] |

Table 3 - Changes is plasma tryptophan levels [micromols/l] in patients taking 3 gram of nicotinamide daily for 2 months.

| Patient | Days of Treatment | Baseline Plasma Tryptophan | Final Plasma Tryptophan | Change in Plasma Tryptophan |
|---|---|---|---|---|
| 1. | 57 | 31.1 | 52.9 | + 70.1% |
| 2. | 61 | 53.4 | 82.3 | + 54.1 % |
| 3. | 63 | 62.0 | 75.1 | + 21.1% |
| 4. | 60 | 51.0 | 66.5 | + 30.4% |

Table 4 - Changes in non-tryptophan plasma amino acid levels in HIV infected patients taking 3 grams/day of oral nicotinamide.

| Patient | Days of Treatment | Baseline Plasma Methionine | Final Plasma Methionine | Change in Plasma Methionine |
|---|---|---|---|---|
| 1. | 57 | 19.8 | 18.3 | - 7.6% |
| 2. | 61 | 15.6 | 17.1 | + 9.6 % |
| 3. | 63 | 34.3 | 24.4 | - 28.9% |
| 4. | 60 | 18.3 | 20.4 | + 11.5% |

| Patient | Days of Treatment | Baseline Plasma Lysine | Final Plasma Lysine | Change in Plasma Lysine |
|---|---|---|---|---|
| 1. | 57 | 218.7 | 111.1 | - 49.2% |
| 2. | 61 | 97.7 | 141.2 | + 44.5 % |
| 3. | 63 | 251.8 | 162.7 | - 34.5% |
| 4. | 60 | 191.8 | 129.1 | - 32.7% |

| Patient | Days of Treatment | Baseline Plasma Cysteine | Final Plasma Cysteine | Change in Plasma Cysteine |
|---|---|---|---|---|
| 1. | 57 | 48.3 | 54.7 | + 13.3% |
| 2. | 61 | 27.0 | 28.8 | + 6.6 % |
| 3. | 63 | 35.6 | 39.1 | + 9.8% |
| 4. | 60 | 75.5 | 61.3 | -18.8% |

Table 4 (cont.)

| Patient | Days of Treatment | Baseline Plasma Taurine | Final Plasma Taurine | Change in Plasma Taurine |
|---------|-------------------|-------------------------|----------------------|--------------------------|
| 1.      | 57                | 46.3                    | 68.8                 | + 48.6%                  |
| 2.      | 61                | 76.2                    | 87.4                 | + 14.4 %                 |
| 3.      | 63                | 92.1                    | 69.7                 | - 24.3%                  |
| 4.      | 60                | 80.6                    | 61.6                 | - 23.6%                  |

TREATMENT OF RETROVIRUS INDUCED DERANGEMENTS WITH NIACIN COMPOUNDS

FIELD OF INVENTION

This invention relates to the treatment of mammals chronically infected with retroviruses, such as human immunodeficiency virus [HIV].

BACKGROUND

Retroviruses lead to chronic infection in mammals. Retroviruses are packets of infectious nucleic acids (i.e. genetic material) surrounded by a protective protein coat. Retroviruses are incapable of generating metabolic energy or synthesizing proteins, and thus are characterized by dependence on living cells for replication and proliferation. A retrovirus contains three enzymes: (1) reverse transcriptase, (2) protease, and (3) integrase. Current antiviral drug therapy focuses on the inhibition of reverse transcriptase and protease enzymes.

HIV is a prototypic retrovirus that causes the acquired immunodeficiency syndrome [AIDS] in humans and related primates. Worldwide, AIDS has claimed over 11 million lives. HIV currently infects more than 30 million people. Since the first reported cases of AIDS almost 20 years ago, the medical community has learned much about this retroviral disease and its diverse manifestations. A number of clinical manifestations of HIV infection, however, remain unexplained despite the efforts of the medical community to discover their etiology.

The Center for Disease Control and Prevention (the "CDC") has developed a "case definition" of the specific findings which, if present in a person with HIV, define AIDS. See Center for Disease Control and Prevention, 1993 *Revised Classification System for HIV Infection and Expanded Surveillance Case Definition for AIDS Among Adolescents and Adults*, MMWR Morb Mortal Wkly Rep, 41(RR-17): 1–19(1992). The CDC's case definition falls into three broad categories: (1) CD4 immune cell depletion, (2) opportunistic infections, and (3) malignancies.

In addition to the case definition of AIDS, a number of metabolic changes are associated with this chronic infection. Among them are alterations in the circulating concentrations of amino acids. Amino acids are often referred to as the building blocks of proteins. Of the common amino acids, ten amino acids are "essential." The essential amino acids are those which the body cannot synthesize and therefore must be obtained directly through the diet.

Tryptophan, an essential amino acid, is known to be depleted during HIV infection. The body utilizes dietary-derived tryptophan for several important biochemical functions, including: (1) as a building block in the synthesis of proteins, (2) as a precursor of niacin and nicotinamide adenine dinucleotide [NAD], and (3) as a precursor of serotonin. Attempting to simply replete plasma tryptophan directly through pharmacologic doses of tryptophan is not advisable given the history of patients developing "eosinophillia myalgia syndrome."

Chronic retroviral infections lead to an ongoing metabolic burden on the infected subject. This burden in HIV infection includes: (1) the turnover of CD4 cells, (2) the disturbance of lipid metabolism, (3) the depletion of serotonin, (4) the depletion of plasma tryptophan [as discussed above], and (5) the depletion of intracellular NAD. The infection, over the course of months, leads to immunodeficiency (marked by CD4 depletion) and opportunistic infections. The infection also leads to a metabolic disease state marked by a number of other manifestations, including a non-specific "wasting syndrome" and the specific disturbances and depletions previously mentioned in this paragraph.

Presently, no cure exists for HIV infection. Current treatments for HIV infected patients tend to focus on agents which inhibit two viral enzymes: the HIV-reverse transcriptase [reverse transcriptase inhibitors] or the HIV-protease [protease inhibitors]. Such agents include among others, ZDV (zidovudine), DDI (2'-3'-dideoxyinosine), and DDC (2'-3'-dideoxycytidine), each of which blocks the HIV proliferation in cells (ZDV, DDI, DDC and other such agents are referred to as the "licensed antivirals"). Unfortunately, the inhibition which occurs with the licensed antivirals is incomplete. Over time, HIV becomes resistant to the licensed antivirals. This resistance can result in a resumption of progressive immune system destruction.

Zidovudine, a licensed antiviral compound, is the only compound known to replete plasma tryptophan in HIV infected persons. However, zidovudine which is a reverse transcriptase inhibitor, causes a number of side effects including headache, nausea, and bone marrow suppression. Furthermore, HIV can develop resistance to Zidovudine, an event which would be expected to result in recurrent tryptophan depletion.

Since HIV depletes plasma tryptophan and since this essential amino acid is required in a range of biologically necessary tasks, replenishing plasma tryptophan is essential in maintaining overall health in the HIV infected state. Although the antiviral drug zidovudine leads to an increase in plasma tryptophan in HIV infected persons, this reversal would be expected to last only so long as virus inhibition persists, and antiviral drug failure is expected with time given the incomplete nature of the drug's inhibitory effect. Niacin, as an agent to reverse infection-induced metabolic changes, works on the host side of the virus-host interaction and therefore would not be subject to the same risk of eventual viral drug resistance.

BRIEF SUMMARY OF THE INVENTION

This invention inhibits adverse metabolic and immunologic effects associated with chronic retroviral infections such as HIV by using niacin compounds, such as nicotinamide or nicotinic acid, to inhibit the depletion of tryptophan and to induce the restoration of intracellular nicotinamide nucleotides, such as nicotinamide adenine dinucleotide [NAD], in patients with retroviral infections.

More particularly, this invention relates to the oral use of pharmacologic doses of niacin compounds in persons with HIV infection in order to reverse or prevent deleterious metabolic consequences of the infection.

Another object of the invention is to inhibit adverse effects of HIV infection by combining the method of this invention with known HIV inhibitors, such as reverse transcriptase inhibitors, protease inhibitors, and others.

The invention provides a method of administering a therapeutically effective amount of niacin compounds to a patient with a chronic retroviral infection such as HIV, the etiological agent clinically associated with AIDS.

BRIEF DESCRIPTION OF THE SEVERAL VIEWS OF THE DRAWINGS

Table 1—Baseline Characteristics of Niacin Study Patients. Illustrates the immunological status as measured by CD4 count, the concomitant use of antiviral medications, and the presence of co-infections. Niacin worked to improve tryptophan status in all four patients across this range of baseline infectious disease related findings.

Table 2—Baseline Dietary intake of Niacin Study Patients. Illustrates the range of baseline dietary intake of tryptophan and niacin compounds. The amounts were determined by dietary recall survey, and demonstrate that tryptophan and niacin were not deficient in the baseline diet of these patients, and that the pharmacological dose of niacin used in the study was significantly higher than all participant's baseline intake.

Table 3—Changes in plasma tryptophan levels [micromols/l] in patients taking 3 gram of nicotinamide daily for 2 months. The increase in the levels of this essential amino acid despite the unchanged dietary intake of tryptophan is consistent with decreased metabolic shunting of essential tryptophan towards niacin in HIV infected persons.

Table 4—Changes in non-tryptophan plasma amino acid levels in HIV patients taking 3 grams/day of oral nicotinamide. The four amino acids include two essential amino acids [methionine and lysine] and two nonessential amino acids [cysteine and taurine]. In all four cases there is no discernible pattern of change with this intervention, supporting the observation that the effect of pharmacological doses of niacin on plasma tryptophan is a specific and important intervention against the metabolic disruption caused by HIV infection.

DESCRIPTION

The invention is a method for treatment of HIV infected persons with niacin administered in an amount effective to combat plasma tryptophan depletion. This invention is useful for any mammal infected with a retrovirus, including HIV. Through administration of a pharmacological dose of niacin, the retrovirus-infected subject's systemic tryptophan depletion will be reversed.

Niacin refers to either of two chemically related compounds: nicotinamide or nicotinic acid. Niacin may be administered orally, parenterally, rectally, or with any pharmaceutically accepted adjuvant or carrier. The administration and effects of niacin have undergone extensive study in the fields of diabetes and hypercholesterolemia. (See, e.g., Petley A, et al, *The Pharmacokinetics of Nicotinamide in Humans and Rodents, Diabetes,* 44: 152–155 (1995); and DiPalma J R and Thayer W S, *Use of Niacin as a Drug,* Annu. Rev. Nutr., 11: 169–87, (1991)). Niacin, or vitamin B3, is the common name for both nicotinic acid, i.e., $C_6H_5NO_2$, (pyridine-3-carboxylic acid) or nicotinamide, i.e., $C_6H_{60}N_2$ (3–10 pyridinecarboxamide).

Niacin is a precursor to the biosynthesis of nicotinamide adenine dinucleotide (NAD) and nicotinamide adenine dinucleotide phosphate (NADP). Nicotinamide nucleotides (NAD and NADP) participate in a wide array of oxidation-reduction reactions catalyzed by dehydrogenase or oxidoreductase enzymes. Virtually every aspect of cellular metabolism involves NAD/NADH or NADP/NADPH dependent reactions. In absence of sufficient supplies of nicotinamide nucleotides or niacin precursors for nicotinamide nucleotide biosynthesis, cellular functions and life itself would be impaired. (DiPahna J R and Thayer W S, *Use of Niacin as a Drug,* Annu. Rev. Nutr., 11: 169–87, (1991)). The body can readily convert nicotinic acid to nicotinamide and both are expected to produce the desired therapeutic effect of combating plasma tryptophan depletion.

For this invention, it is preferred to administer niacin in "pharmacologic doses." A vitamin compound is considered a "drug," not a "nutrient," when: [1] the ingested dose exceeds the dose required for nutrient function, and [2] a pharmacologic action distinct from nutrient function is achieved. Maintaining plasma tryptophan is not a nutrient function of niacin; rather, it is a pharmacological action of niacin in retrovirally infected subjects.

All vitamins fill a nutrient function whereby a sufficient amount of the vitamin compound is required in the diet to fulfill normal metabolic needs. The body normally requires 12–18 milligrams of niacin per day to carry out the coenzyme function which defines niacin as a vitamin. The Recommended Daily Allowance [RDA] of niacin is approximately 13–20 milligrams per day. Therefore, a non-pharmacologic dose of niacin, where niacin acts as a vitamin or nutrient compound, is approximately 20 milligrams a day or less.

The use of pharmacologic doses of niacin is distinct from the vitamin or nutrient use of niacin. (DiPalma J R and Thayer W S, *Use of Niacin as a Drug,* Annu. Rev. Nutr., 11:169–87, (1991)). Niacin's pharmacologic use can be distinguished from its non-pharmacologic (or physiologic) use by the pharmacodynamic action of the compound. Pharmacodynamic action begins when the nutrient function of niacin is complete. The maintenance of plasma tryptophan in the face of (1) retrovirus infection, and (2) normal or supernormal niacin levels is the distinct pharmacodynamic action described here.

A pharmacological dose of niacin generally occurs at a dose of about 100 milligrams per day, about 5 times the recommended daily allowance [RDA]. Niacin is safe in doses greater than 100 mg in persons with HIV, and doses of greater than 100 mg should also cause a retrovirus-infected patient to undergo a reverse systemic tryptophan depletion.

Because pharmacologic doses of niacin alleviate the drive to deplete plasma tryptophan, tryptophan depletion may represent a metabolic shunt towards niacin production. (See Murray, Niacin as a Potential AIDS Preventative Factor, Medical Hypotheses 53(5), 375–379 (November 1999), which is incorporated herein by reference.) In addition, because the essential amino acid tryptophan cannot be synthesized in the body, any agent which increases in the circulating concentrations of tryptophan in HIV infected persons presumably does so by diminishing the metabolic demands on the available supply.

The preferred embodiment of this invention is to administer a mammal infected with a retrovirus with niacin. The preferred method of administration is oral administration. The preferred dose is 500 milligrams of niacin per day in the form of nicotinamide.

The following EXAMPLE is presented to more fully illustrate the preferred embodiment of the invention. The example should not be construed to limit the scope of the invention and is to be understood merely for the purpose of illustration.

EXAMPLE

Clinical Trial of Niacin in HIV Infected Persons

Four HIV infected persons participated in a trial of niacin in the form of nicotinamide. The participants were at various stages of their HIV infection as judged by their CD4 counts which ranged from 0 to 620 [see table 1]. The participants were receiving either a stable regimen of anti-viral drugs [i.e. anti-HIV drugs] for a period greater than one year or were not taking any anti-viral drugs. Two of the participants had known co-infections infections typical of HIV infected persons. Each participant took 3 grams of nicotinamide per day for 2 months. This treatment was not associated with any adverse side effects. Each participant's plasma tryptophan was measured prior to treatment and at the end of treatment [see table 3]. The average increase of plasma tryptophan of all participants was 43.9%. This change in tryptophan concentration was statistically significant with a calculated p value of p=0.0112 [using paired t-test]. The study also measured 4 other plasma amino acids which are listed in table 4. All amino acid concentrations were measured by High Performance Liquid Chromotography [HPLC]. There was no significant change in the plasma amino acid concentrations other than tryptophan. As demonstrated in tables 3 and 4, only plasma tryptophan changed in a statistically significant manner.

The details of the invention have been set forth in the accompanying description and example above. Although any methods and materials similar or equivalent to those described herein can be used in the practice or testing of the present invention, the preferred methods and materials have been described. Other features, object, and advantages of the invention will be apparent from the description and from the claims. In the specification and the claims, the singular forms include plural referents unless the context clearly requires otherwise. Unless defined otherwise, all technical and scientific terms used herein have the same meaning as commonly understood by one of ordinary skill in the art to which this invention belongs. All patents and publications cited in this specification are incorporated by reference.

What is claimed is:

1. A method of increasing systemic tryptophan comprising the administration of an effective amount of niacin for increasing systemic tryptophan to a patient in need of an increase in systemic tryptophan wherein the patient is infected with a retrovirus and wherein the patient has a diet that includes at least the RDA (recommended daily allowance) of niacin and Tryptophan, wherein the effective amount is approximately 3 gram per day.

2. The method of claim 1 wherein the effective amount is sufficient to raise the intracellular levels of nicotinamide adenine dinucleotide [NAD] in persons with HIV infection.

3. The method of claim 1 wherein the effective amount is sufficient to replete nicotinamide nucleotide precursors [NAD].

4. The method of claim 1 wherein the effective amount of niacin is administered to persons with HIV and other co-infections.

5. The method of claim 1 wherein the effective amount of niacin is administered in combination with antiviral medications selected from the group consisting of reverse transcriptase inhibitors and protease inhibitors.

6. The method of claim 1 wherein the effective amount is administered in combination with other treatments for HIV infection to improve the metabolic status of an infected patient.

7. The method of claim 1 wherein the effective amount of niacin is administered in combination with antiviral medications.

8. The method of claim 1 wherein the administration occurs by the method selected from the group consisting of oral administration, parenteral administration, rectal administration, pharmaceutical adjuvant administration and pharmaceutical carrier administration.

9. The method of claim 1 wherein the niacin is in the form selected from the group consisting of nicotinamide and nicotinic acid.

10. The method of claim 1 wherein dietary intake of niacin is less than 100 milligrams.

11. The method of claim 1 wherein dietary intake of tryptophan is less than 1.44 grams.

* * * * *